United States Patent
Collyer et al.

[11] Patent Number: 5,973,221
[45] Date of Patent: Oct. 26, 1999

[54] WOUND DRESSING

[75] Inventors: Graham John Collyer, Padfield; Paul Alan Gray, Droylsden, both of United Kingdom

[73] Assignee: Seton Healthcare Group PLC., Avon, United Kingdom

[21] Appl. No.: 08/473,452

[22] Filed: Jun. 7, 1995

[30] Foreign Application Priority Data

Jun. 8, 1994 [GB] United Kingdom .................... 9411429

[51] Int. Cl.⁶ .................................................. A61F 13/00
[52] U.S. Cl. .................................. 602/46; 602/48; 602/54; 602/56
[58] Field of Search ................................ 602/46, 54, 57, 602/47, 48, 56, 59

[56] References Cited

U.S. PATENT DOCUMENTS

| Re. 31,886 | 5/1985 | Hodgson .............................. 602/54 X |
| 2,735,426 | 2/1956 | Claydon .................................. 602/46 |
| 5,407,442 | 4/1995 | Karapasha ............................. 604/359 |

FOREIGN PATENT DOCUMENTS

| 646400 | 5/1991 | Australia .................................. 602/46 |
| 651252 | 5/1993 | Australia .................................. 602/46 |
| 0106439 A1 | 8/1983 | European Pat. Off. . |
| 0117438 A2 | 1/1984 | European Pat. Off. . |
| 1440191 | 6/1976 | United Kingdom . |
| 2102012 | 7/1981 | United Kingdom . |
| 2093702 | 2/1982 | United Kingdom . |
| 2228682 | 2/1989 | United Kingdom . |
| 2253628 | 2/1992 | United Kingdom . |
| WO 91/01707 | 2/1991 | WIPO . |

*Primary Examiner*—Jerome W. Donnelly
*Assistant Examiner*—Kim M. Lee
*Attorney, Agent, or Firm*—Duane, Morris & Heckscher LLP

[57] ABSTRACT

A wound dressing for moist wounds is formed from a body layer (1) with a wound-contacting layer (3) attached to an inner surface and a barrier backing layer (2) attached to an outer surface. The body layer (1) is a resiliently compressible moisture-absorbent polyurethane foam film. The wound-contacting layer (3) is preferably a hydrophilic moisture permeable foam film. The barrier backing layer (2) is a liquid and bacteria proof gas-permeable foam

14 Claims, 3 Drawing Sheets

WOUND DRESSING

FIELD OF THE INVENTION

This invention relates to a wound dressing.

BACKGROUND OF THE INVENTION

It is known to use resiliently compressible foamed plastics material for wound dressings. This material can permit comfortable application of pressure even on curved or other non-planar body surfaces. Also the material can have good absorption properties suited to use with moist wounds.

It is important or desirable to have surface properties which for the wound-facing inner surface permit easy flow of moisture into the dressing whilst avoiding sticking to the wound, and for the outer surface provide at least to a certain extent, a waterproof breathable barrier. However problems arise in connection with the provision of satisfactory surface properties in the context of foam material. In particular, modification of the surfaces of the foam material, by treatment thereof, or by application of surface layers thereto, tends to give rise to distortion of the foam material as the foam absorbs moisture and swells. Distortion is disadvantageous because it disrupts even application of pressure and can disturb healing of the wound. Also, air pockets may be formed which provide sites for bacterial growth.

British Patent 1417962 describes the use of a non-reticulated polyurethane foam which is modified at the wound-facing inner surface, by application of heat and pressure, to give a layer of collapsed cells, which layer is soft, pliant and facilitates flow of moisture from the wound into the body of the foam material.

A development of this known structure, involving the use of a body of open-celled hydrophilic foam is described in WO 92/13576. This construction facilitates flow of moisture at a relatively high rate suited to use with very moist wounds. However, considerable swelling and consequent distortion can arise.

An object of the present invention is to provide a wound dressing which incorporates an absorbent foam layer and has good surface properties yet which has good dimensional stability and a reduced tendency to distort on absorption of moisture.

SUMMARY OF THE INVENTION

According to the invention therefore there is provided a wound dressing comprising a body layer of a resiliently compressible moisture-absorbent foam material, said body layer having an outer surface with a layer providing a barrier to liquid applied thereto, and an inner wound-facing surface with a wound-contacting layer applied thereto, said wound-contacting layer comprising an attached layer of moisture permeable material, and said barrier layer comprising an attached layer of a gas permeable material which has at least a reduced moisture permeability relative to the body layer.

DETAILED DISCUSSION

Figure 1:
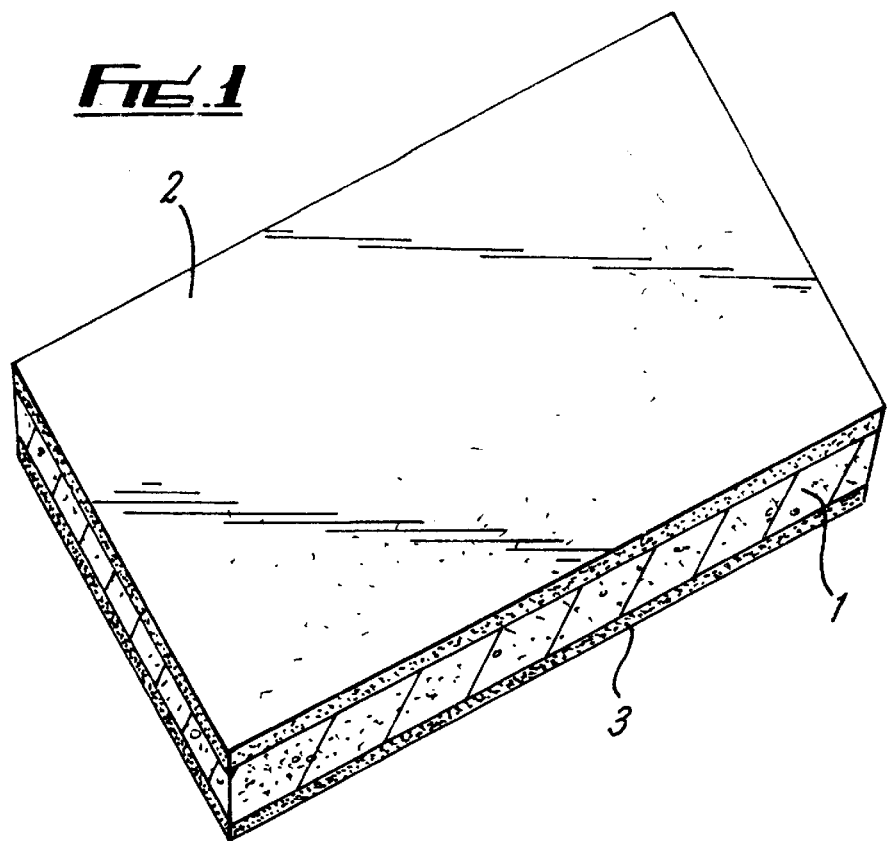
FIG. 1 is a diagrammatic perspective view of one constructional form of the inventive wound dressing.
Figure 5:
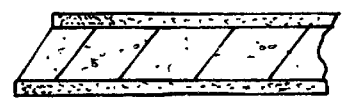
FIGS. 3–8 illustrates sectional details of alternative shaped edges of the dressing.

With this arrangement the foam body layer can permit comfortable application of pressure to a wound whilst absorbing significant quantities of moisture from the wound, the inner surface layer can give non-stick wound contact with controlled flow of moisture into the body layer, and the outer surface layer can give resistance to ingress of liquid through the outer surface. At the same time, the attached inner and outer surface layers can maintain dimensional stability and prevent or limit distortion after absorption of moisture.

With regard to the foam material of the body layer, any suitable material may be used. Preferably a polyether polyurethane foam having hydrophilic characteristics is used. This kind of foam can be readily absorbent and physiologically compatible and can demonstrate good resilience and compressibility suited to the comfortable application of even, sustained pressure. Suitable foams are described in WO 92/13576.

The body layer may have a thickness in the range say 3 to 20 mm particularly 8 to 12 prior to compression. A typical useful thickness is 11 mm. A preferred thickness range after compression is 3 to 12 mm, particularly 7–10.

The body layer is the functional liquid absorbing part of the dressing. Liquid exudate from the wound is absorbed into the body part. The absorbed liquid is retained against free flow out of the dressing but it is kept away from the wound to facilitate healing and evaporates at a controlled rate, as a consequence of the properties of the body layer, and also the wound-contacting surface layer.

With regard to the barrier layer, this also may be formed from any suitable material. The function of the barrier layer is to prevent or restrict flow of liquid therethrough whilst permitting passage of gas or vapour so that liquid in the body layer can gradually evaporate from the dressing.

It is preferred that the barrier layer should also have the capability of preventing or at least appreciably restricting ingress of bacteria.

A high density closed cell polyurethane foam is particularly suitable for the barrier backing layer. Any other suitable material may also be used which provides similar properties to this closed cell polyurethane foam, for example, polyester films, polyether block amide films, and combinations of these, which may be rendered breathable bacterial barriers by mechanical or chemical processes.

A preferred thickness range is 0.2 to 0.8 mm. If the layer is too thin it will not be possible to trap bacteria. If it is too thick there will be little or no evaporation through the layer. A thickness of 0.4 mm is particularly useful.

The backing layer may be attached to the body layer in any suitable manner. In a preferred arrangement the backing layer is heat bonded to the body layer by application of heat and pressure with a heated platen or the like, or a roller. The backing layer may also be bonded using a suitable adhesive (as for example is used in the case of island dressings), although this may interfere with the moisture vapor permeability to a certain extent. Suitable adhesives are isooctyl acrelate, ethyleneoctyl acrelate, acrylic acid terpolymer and composites of these. The adhesive may also contain additives such as povidone iodine, chlorhexidine or chemical indicators.

The backing layer provides restricted or controlled flow of liquid, gas, vapor and bacteria as mentioned above. Also it acts to maintain dimensional stability for the body layer. As the body layer tends to expand and swell on absorption of liquid, the backing layer helps prevent or restrict distortion of the dressing.

With regard to the wound contacting layer this may also be formed from any suitable material having requisite properties of moisture permeability and wound compatibility. The layer is preferably hydrophilic A polyether or polyesterflexible polyurethane foam is suitable. A homogenous hydrophobic foam may be used which is rendered hydrophilic by heat treatment e.g. during heat bonding thereof to the body layer.

The wound-contacting layer facilitates controlled flow of liquid exudate from the wound into the absorbent body layer of the dressing. The properties of the wound contact layer preferably minimize or prevent swelling and avoid excessive moisture retention. The layer preferably permits slight moisture retention so that it has a reduced tendency to stick to or otherwise interfere with the wound, and also the layer can retain its structure and dimensions and help maintain the dimensional stability of the dressing.

Also, controlled flow of liquid from the wound into the body layer can be of importance with regard to wound healing and avoidance of dressing distortion. Flow of liquid should be at a high enough rate to prevent build up of excess liquid at the surface of the wound, but it should not be so high that the wound becomes too dry and the body structure excessively wet. The wound contacting layer preferably should maintain a very small amount of moisture at the wound surface to provide the wound with a moist healing environment.

Suitably the wound-contacting layer may be formed from a collapsed or compressed polyurethane foam having a thickness of say 1 to 12 mm prior to compression. If the wound contacting layer is too thick there is a greater chance of undesirable lateral strike through of exudate.

The wound-contacting layer may be attached to the body layer by heat bonding by application of heat and pressure e.g. with a heated platen or the like, or a roller. The wound-contacting layer may also be attached by the use of adhesives, ultra sonic welding, infra red welding or otherwise.

The barrier layer and the wound-contacting layer may be attached to the body layer in separate operations or, alternatively, simultaneously, for example by passing the layers between rollers.

The dressing may be formed in continuous strip or sheet form and may then be cut to give individual dressings of a desired size and shape.

If desired any or all of the layers, particularly the body layer may be impregnated with any suitable substance such as an antiseptic, e.g. povidone iodine or chlorhexidine, or other medicament or chemical indicators.

Individual dressings may be sterilized by irradiation or otherwise, e.g. after packaging.

The wound dressing may be shaped and provided with additional structures or materials such as adhesive portions, as desired and in accordance with the intended use. Thus, for example, the dressing may be oblong with square or rounded corners, tear-drop, circular or oval. The edges of the dressing may be square-cut, rounded, bevelled or crimped etc. using a number of methods for example, a heated platen with pressure, high frequency welding/cutting or ultra-sonic welding/cutting.

The invention will now be described further in the following Example.

An example wound dressing according to the invention is made from an absorbent body layer with films applied to opposite faces thereof.

The body layer comprises a resiliently compressible 'soft-feel' layer of polyether polyurethane foam having a thickness of 11 mm in its relaxed uncompressed state. The foam is an open-celled hydrophilic material typically made from the following ingredients in parts by weight:

| | |
|---|---|
| Polyether polyol rich in ethylene oxide (polyol 1) | 75 |
| Branched ethylene oxide modified polyether polyol (polyol 2). | 25 |
| Tolylene diisocyanate (T 80/20) | 36.5 |
| Dimethyl ethanolamine (DMEA) | 0.05 |
| Triethylenediamine (TEDA) | 0.12 |
| Polysiloxane-polyoxyethylene block copolymer (cell stabilizer) | 1.20 |
| Water | 3.00 |

Polyol 1 and 2 may be VORANOL CP 1421 and VORANOL CP 4800 (or CP 4810) sold under these trade marks by The Dow Chemical Company. Alternatively polyol 1 and 2 may be DESMOPHEN 7040 and DESMOPHEN 3900 (or 7160 or 7116) sold under these trade marks by Bayer AG.

The hydrophilic properties can be adjusted by adjusting the ethylene oxide content of polyol 1 or by altering the relative ratios of polyols 1 and 2.

Foam density can be varied by adjustment of the water level typically to give a density of 27–31 kg/m$^3$ (typically 30), hardness 45–75 Newtons, nominal tensile strength 70 KPa minimum, nominal elongation at break 150% minimum, nominal compression set 20% max.

The foam body layer may absorb at least ten times its initial weight of liquid.

The foam can be produced as slabstock on conventional foam making machinery and can be cut to size as required for the body layer of the dressing.

A backing layer in the form of a film for application to one surface of the above body layer comprises a layer of predominantly closed cell high density polyether polyurethane foam of a blocked tolylene diisocyanate nature having a thickness of 0.4 mm. Suitably this may be the material sold under the trade mark MEDIFIX 4003 by Adhesive Products Ltd. This material has a pore size of 0.1 mm to 0.3 mm, a density of 325–435 kg/m$^3$ and a tensile strength of 1.276 kg/25 mm. Moisture vapor permeability can range from 500 to 4000 grams/m$^2$/24 hours typical values are in the order of 1200 grams/per m$^2$/24 hours. Preferable values are greater than 1000grams/m$^2$/24 hours.

A wound-contacting layer in the form of a film for application to the opposite surface of the body layer comprises a layer of polyurethane foam (polyether or polyester) having a density within a range of say 12–76 kg/m$^3$ (polyether) or 14–75 kg/m$^3$ (polyester). This is used in a thickness of say 3 to 7 mm.

In general a typical polyether foam is made by selection from the following ingredients with parts by weight:

| | |
|---|---|
| Propylene oxide/ethylene oxide polyether triol | 10–100 |
| Polyoxypropylene triol | 10–100 |
| Tolylene diisocyanate (T 80) | 25–65 |
| Dimethylethanolamine | 0.05–1.2 |
| Triethylenediamine | 0–0.8 |
| Silicone surfactant | 0.3–2.0 |

-continued

| Stannous Octoate | 0.04–1.0 |
| --- | --- |
| Water | 1–5.5 |
| Hydrocarbon blowing agent | 0–20 |

A typical polyester foam is made from the following ingredients:

| Polyester polyol (branched glycol adipate) | 100 |
| --- | --- |
| Tolylene diisocyanate (T 65) | 20–70 |
| Tertiary amine | 0.1–1.0 |
| Surfactant | 0.5–2.0 |
| Water | 1–5.5 |
| Hydrocarbon blowing agent | 0–15 |

A specific formulation for a polyether foam would be:

| Polyol (A) | 100 parts by weight |
| --- | --- |
| Isocyanate (B) | 63.0 parts by weight |
| Index | 11.2° |
| Amine Catalyst (C) | 0.25 parts by weight |
| Amine Catalyst (D) | 0.04 parts by weight |
| Silicone surfactant (E) | 1.30 parts by weight |
| Water | 5.05 parts by weight |
| Tin Catalyst (F) | 0.32 parts by weight |
| Blowing Agent (G) | 10 parts by weight |

Where:
A is a polyether polyol such as ARCOL 1131 sold by ARCO.
B is a tolylene diisocyanate such as SYRANATE T80 sold by Rhone Poulenc.
C is dimethylethanolamine such as DABCO DMEA sold by Air Products.
D is an amine catalyst such as DABCO BL-11 sold by Air Products.
E is a silicone surfactant such as B8234 sold by Goldschmidt.
F is a tin catalyst such as DABCO T9 sold by Air Products.
G is a hydrocarbon blowing agent such as methylene chloride.

Typical physical properties are:
nominal density range 15–19 kg/m$^3$
nominal hardness range 25–45 Newtons
nominal tensile strength 60 KPa minimum
nominal elongation at break 150% minimum
nominal compression set 30% maximum The body layer is united with the wound-contacting layer and the barrier layer on opposite faces and the combination is passed through a heated press. This causes the layers to be laminated together due to fusion at the interfaces between the layers. At the same time the wound-contacting layer is crushed or collapsed so that its thickness reduces to say 1 mm. The thickness of the body layer may reduce to say 10 mm. The lamination process imparts requisite hydrophilic properties to the wound contacting layer.

The resulting laminate is cut to give individual dressings which may be impregnated with medicaments, packaged in sealed enclosures and sterilized by irradiation.

In use the dressing has good, controlled absorbency and high dimensional stability.

The accompanying drawings show a range of applications of the above example dressing.

In the drawings:

FIG. 1 shows a dressing constructed in accordance with the above described Example, having a body layer 1, a backing layer 2, and a wound-contacting layer 3.

Figure 2:
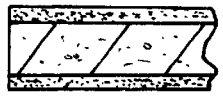
FIG. 2 is a sectional detail of an edge of the dressing of FIG. 1.
Figure 6:
Figure 3:
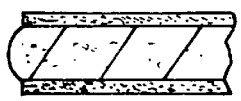
Figure 7:
Figure 4:
Figure 8:

The edge may be straight as shown in FIG. 2, or may be shaped as shown in FIGS. 3–8. The backing and wound-contacting layers 2, 3 may terminate independently at the edge or may be secured together (thermally or otherwise) as shown in FIGS. 6–8.

Figure 9:
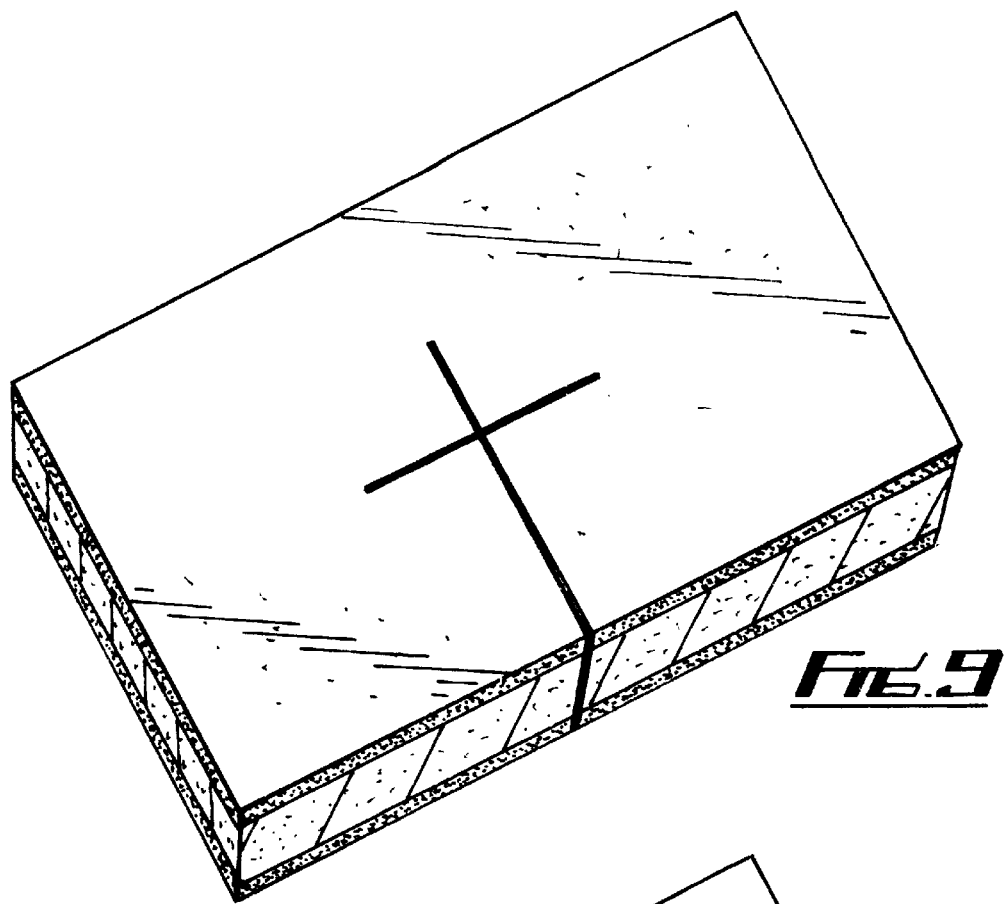
FIGS. 9–10 illustrate diagrammatic perspective views of a modification of the dressing incorporating cross-cuts.
Figure 10:
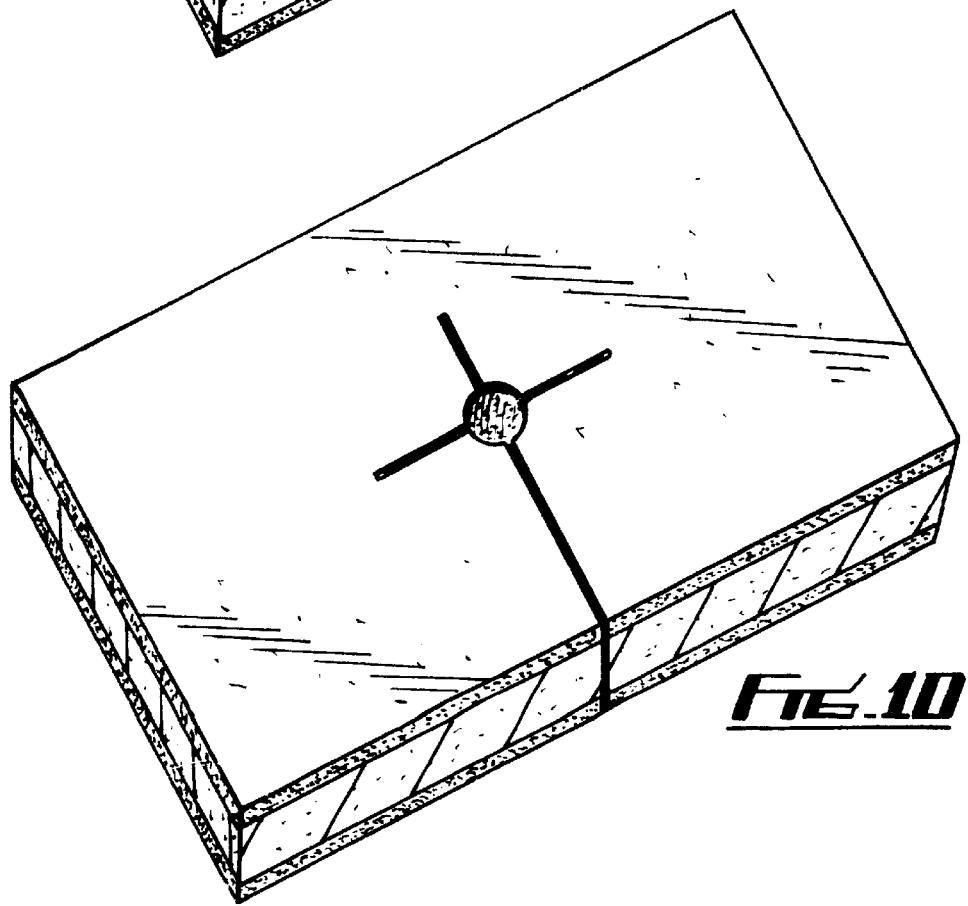

FIG. 9 shows a standard cross-cut, and FIG. 10 shows a cross-cut with hole, formed in a dressing of the kind shown in FIG. 1.

Figure 11:
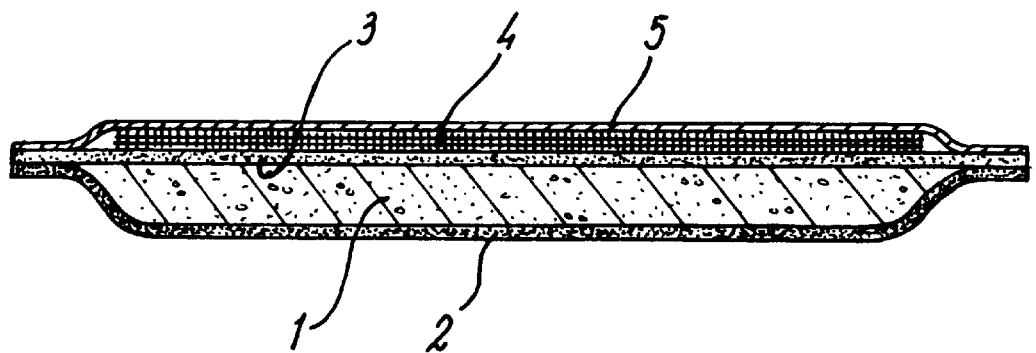
FIG. 11 is a diagrammatic sectional view of a dressing with an active carbon layer.

FIG. 11 shows a dressing of the kind shown in FIG. 8 with an additional layer 4 held in position over the backing layer 3 by means of a retaining layer 5.

The additional layer 4 may be an activated carbon layer comprising a non-woven material with a base composition of viscose/polyester fibre (80 parts by weight), acrylate binder (20 parts by weight) impregnated on both sides with active carbon powder. Typically the base composition may have a nominal weight of 36 gm/m$^2$ and the carbon impregnant 40 gm/m$^2$. The air permeability may be 30 cm$^3$/cm$^2$/sec.

The retaining layer 5 may be an open cell foam material which is a soft flexible polyester or polyether foam, for example of one of the kinds described above with reference to the layers 1 to 3, although other materials may also be used.

The construction of the foam is not critical—its purpose is to hold the carbon layer in position without unduly affecting the moisture permeability of the dressing. Typically the layer 5 may be 3 mm thick with a density of 24–27 kg/m$^3$. The layer 5 may be held by crimp sealing or otherwise to the edge of the dressing.

Figure 12:
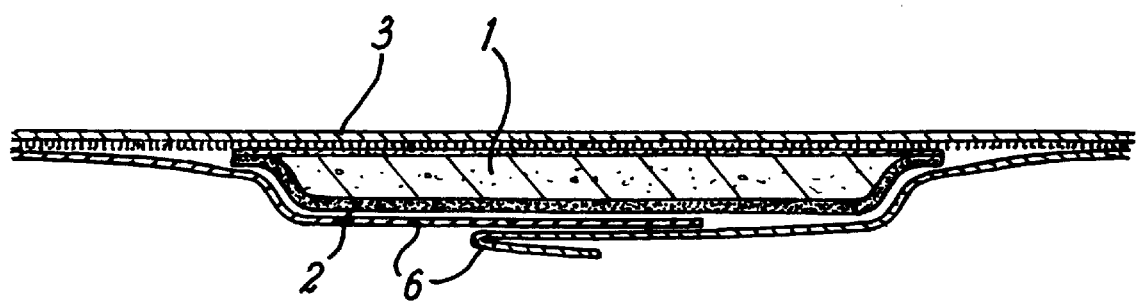
FIG. 12 is a diagrammatic sectional view of an island dressing.

FIG. 12 shows a typical island version of the dressing of FIG. 1 in which the body layer 1 is bonded to the backing layer 2 by means of a layer of skin adhesive which covers the entire surface of the backing layer. The backing layer 2 is much larger than the body layer 1 so that the body layer 1 defines a central island. The wound-contacting layer 3 is heat bonded to the body layer and has its edges crimp sealed (as in FIG. 8) and is adhesively bonded to the backing layer. Pull-off release papers 6 are adhered over the exposed adhesive and cover the body layer.

Usage of the various forms of the dressings shown is as follows:

The base dressing of FIG. 1 is used mainly in the treatment of moderate to heavily exuding wounds, such as leg ulcers, pressure sores, post-operative and traumatic wound sites, burns and skin grafts. The dressing maintains a moist wound micro-environment, removes excess exudate, permits gaseous exchange, provides thermal insulation, avoids trauma at dressing changing, is impermeable to micro-organisms and is free from particular and toxic contaminants, the backing layer prevents strikethough of exudate and reduces the risk of secondary infection.

The tracheostomy and cannulae dressing of FIG. 9, 10 is used as a dressing for tracheostomy and provides protection and cushioning over the site of intubation and cannula insertion procedures and external bone fixators. The cross-cut or key hole cut design fits closely around tubes, cannulae or pins used in invasive medical procedures.

The dressing with activated carbon of FIG. 11 is used in the treatment of moderate to heavy exuding wounds designed to absorb and neutralice offensive odours, and is particularly useful for the treatment of infected malodorous wounds. The backing layer ensures that the activated carbon layer remains dry and effective throughout the period of use.

The island dressing of FIG. 12 is a water resistant dressing having an adhesive covered perimeter to hold the pad of the dressing securely in place without the need for additional tapes or retention bandage. It resists faecal and urinary contamination and is particularly useful for sacral sores on incontinent patients and on cutaneous wounds.

The dressings can be used as an antiseptic impregnated dressing for the prevention of infection in wounds including ulcers, burns and cuts. It is highly effective against the complete spectrum of potentially pathogenic microorganisms including gram-positive and gram-negative bacteria, viruses, fungi, protozoa and spores. The antiseptic ingredient is placed on the wound contacting surface of the dressing in the form of a solution, cream or paste etc. or maybe contained within the layers of the dressing in the form of, for example a powder.

Variations of the antiseptic may be povidone iodine, silver sulpha-diazine, zinc based material, chlorhexidine, cetramide or combinations of the above etc.

A particularly useful product may be produced by using an alcoholic solution containing povidone iodine applied thinly across the wound contacting surface and dried prior to packaging. On application to an exuding wound, the povidone iodine shall be released and the desired properties maintained.

A hydrogel may be applied to the wound-contacting surface and kept moist by virtue of sealed packaging.

The dressing described above in the Example is highly absorbent with good dimensional stability and resistance to bacterial strike-through.

The performance of the dressing was compared with foam of the kind described in British Patent 1417962 (trade mark Lyofoam). The dressing was found to absorb almost twice as much liquid for the same sized body of material.

Using thicker materials for the dressing it is possible to absorb more liquid. However heat bonding of the layers may then become difficult and adhesive boding may then be necessary or preferred.

A thick body of foam material, say 20 mm, may be used for high liquid volumes, whereas a thin body, say 5 mm, may be used on light to moderate exuding wounds.

The foam formulation for the foam body in the Example contains large amounts of ethylene oxide groups to improve liquid absorbency. Improved liquid.absorbency can also be achieved by using surfactants, although the use of large amounts of surfactants is undesirable since the surfactant may be transmitted or absorbed in the wound to interfere with wound healing.

It is of course to be understood that the invention is not intended to be restricted to the details of the above embodiment which are described by way of example only.

We claim:

1. A wound dressing comprising a body layer of a resiliently compressible moisture-absorbent foam material, said body layer having an outer surface with a backing layer providing a barrier to liquid applied thereto, and an inner wound-facing surface with a wound-contacting layer applied thereto, said wound-contacting layer comprising an attached layer of a dimensionally stable moisture permeable foam material to control flow of liquid exudate from the wound through said moisture permeable foam material to said moisture-absorbent foam material of said body layer, and said barrier backing layer comprising an attached layer of gas permeable material which has at least a reduced moisture permeability relative to the body layer, said body layer being substantially thicker than said backing and wound-contacting layers.

2. A dressing according to claim 1 wherein the body layer is formed from a hydrophilic polyether polyurethane foam.

3. A dressing according to claim 1 wherein the thickness of the body layer is in the range 3 to 20 mm prior to compression.

4. A dressing according to claim 1 wherein the barrier backing layer is a high density closed cell polyurethane foam.

5. A dressing according to claim 1 wherein the thickness of the barrier backing layer is in the range 0.2 to 0.8 mm.

6. A dressing according to claim 1 wherein the barrier backing layer is heat bonded to the body layer.

7. A dressing according to claim 1 wherein the barrier backing layer is adhesively bonded to the body layer.

8. A dressing according to claim 1 wherein the wound contacting layer is a collapsed or compressed polyurethane foam.

9. A dressing according to claim 1 wherein the wound contacting layer has a thickness of 1–12 mm prior to compression.

10. A dressing according to claim 1 wherein the wound contacting layer is heat bonded to the body layer.

11. A dressing according to claim 1 wherein at least one layer is impregnated with an antiseptic.

12. A dressing according to claim 1 which is an island dressing wherein the barrier backing layer has an adhesive coated surface and the body layer and wound contacting layer are bonded in position on an island centrally on said surface.

13. A dressing according to claim 1 further including an active carbon layer retained on the outer surface of the barrier backing layer by an overlying retaining layer.

14. A dressing according to claim 13 wherein the retaining layer is formed from a permeable foam material.

* * * * *